United States Patent [19]
Oxford

[11] Patent Number: 5,698,432
[45] Date of Patent: Dec. 16, 1997

[54] VACCINES AND METHODS FOR THEIR PRODUCTION

[75] Inventor: John Sidney Oxford, London, England

[73] Assignee: Retroscreen Ltd., London, England

[21] Appl. No.: 729,135

[22] Filed: Oct. 11, 1996

Related U.S. Application Data

[63] Continuation of Ser. No. 327,142, Oct. 21, 1994, abandoned, which is a continuation of Ser. No. 884,347, May 18, 1992, abandoned.

[30] Foreign Application Priority Data

May 17, 1991 [GB] United Kingdom ............... 9110808

[51] Int. Cl.$^6$ .......... A61K 39/21; A61K 39/12; A61K 39/00; C12N 7/04
[52] U.S. Cl. .......... 435/236; 435/238; 435/239; 424/208.1; 424/188.1; 424/204.1; 424/184.1
[58] Field of Search .............. 424/184.1, 188.1, 424/204.1, 208.1; 435/236, 238, 239

[56] References Cited

U.S. PATENT DOCUMENTS

| | | | |
|---|---|---|---|
| 3,674,864 | 7/1972 | Angellucci | 424/90 |
| 4,036,952 | 7/1977 | Bauer et al. | 424/89 |
| 4,086,134 | 4/1978 | Jarrett et al. | 195/1.2 |
| 4,101,652 | 7/1978 | Bonati | 424/49 |
| 4,452,734 | 6/1984 | Larson et al. | 424/89 |
| 4,530,831 | 7/1985 | Lütticken et al. | 424/89 |
| 4,645,666 | 2/1987 | Manning et al. | 424/89 |
| 4,806,350 | 2/1989 | Gerber | 424/88 |

OTHER PUBLICATIONS

Webster, et al, 1966, "Influenza virus subunit vaccines . . . " J. Immunol. 96(4):596–605.

Quinnan, et al, 1986, "Inactivation of human T–cell . . . " Transfusion 26(5):481–483.

Cohen, 1993, "Jitters Jeopardize AIDS Vaccine Trials" Science 262:980–981.

Fox, 1994, "No Winners Against AIDS" BioTechnology 12:128.

Shek, et al, 1982, "Immune response mediated by liposone . . . ", Immunology 47:627–632.

Kersten, et al, 1988, "Influence of presentation form . . . " Technological Advances in Vaccine Dev. A.R. Liss, Inc. pp. 517–526.

Haynes, 1993, "Scienticfic and Social Issues of Human . . . " Science 260:1279–1286.

Butini, et al, 1994, "Comparative analysis of HIV–Speciftic . . . " Abstract J306, J. Cell. Biochem, Suppl. 18B.

O.N. Fellowes; *Comparison Of the Inactivation and Antigenicity Of Foot–and–Mouth–Disease Virus By Acetylethyleneimine and By Combined Effect Of Ultraviolet Light and β–Propiolactone*; vol. 95, No. 6, 1966; The Journal of Immunology, U.S.A.

*Primary Examiner*—Lynette F. Smith
*Attorney, Agent, or Firm*—Rick Martin

[57] ABSTRACT

The present invention relates to the production of vaccines having improved safety, particularly to a process therefor which allows even an AIDS vaccine to be manufactured, comprising in order, the steps of:

a) treating the virus with a general inactivating agent;

b) deaggregating the virus with a suitable solvent or detergent;

c) treating the virus with an RNA and/or DNA inactivating agent; and d) stabilizing the virus with a suitable cross-linking agent.

13 Claims, No Drawings

VACCINES AND METHODS FOR THEIR PRODUCTION

This application is a continuation of application Ser. No. 08/327,142 filed Oct. 21, 1994 now abandoned, which was a continuation of application Ser. No. 07/884,347, filed May 18, 1992 now abandoned.

BACKGROUND TO THE INVENTION

The present invention relates to vaccines for AIDS which comprise prepared whole virus, methods for the production of such vaccines, and useful adjuvants.

An ideal HIV vaccine would provide a complete and long lasting protective response against all forms of HIV, and would be simple and cost effective in production and administration.

However, despite vaccine development being a top priority of AIDS research since 1984, this ideal has yet to be realised. In fact, it is considered by some to be beyond reach, at least in the short term (Bolognesi, 1991). Other scientific opinion ranges from "Development of a safe vaccine against HIV is likely to be a very difficult task" (Desrosier et al., 1989) through "It is unclear whether any vaccine will be effective against a virus which attacks some of the most important cells of the immune system" (Durda et al., 1990) to "A vaccine is perhaps the best hope for the next century not for this one" (Rees-Mogg, 1991).

Such views arise because the lentiviruses, such as HIV, have developed very successful methods to evade the immune response, such as latency and antigenic variability. For example, HIV was the first human lentivirus to be isolated, and is characterised by a unique morphology of an inner vase-like structure containing the diploid RNA genome, surrounded by an icosahedron core composed of protein sub-units, contained by a lipid membrane through which protrude glycoprotein spikes.

As a result of this evasion, full recovery from infection is never observed in a natural situation and viral persistence results, making the development of a vaccine that completely prevents or eliminates infection extremely unlikely.

In the past, successful vaccines have allowed some infection to occur but still prevented disease. This may also be acceptable in an AIDS vaccine. The problem would then lie in establishing what levels, if any, of infection could acceptably be tolerated without progression to clinical disease.

Fundamental to the design of an AIDS vaccine is a knowledge of the protective components of the immune response against HIV and of how they can be stimulated. Studies on sera and peripheral blood mononucleocyte cells (PBMN) from HIV+ patients (Devash, 1990), and on responses to various peptides in HIV and HIV+ individuals and in animals (Mills, 1990; Zarling, 1986; Durda, 1990) have yielded a wealth of information on the nature of the immune response to HIV and on the important antigenic characteristics of the virus.

Despite this knowledge, researchers are still some way from understanding which responses are necessary for elimination or suppression of virus, and which are potentially enhancing or even immunosuppressive.

Research has been slowed by the lack of good experimental models for testing potential vaccine candidates. Although chimpanzees can be routinely infected with the virus, they do not develop an AIDS-like disease and, therefore, are not ideal for HIV challenge experiments. Also, the chimpanzee model suffers from problems of cost, welfare and availability of both animals and facilities (Gardener and Luciw, 1989).

Other immunodeficiency viruses, such as the simian immunodeficiency virus (SIV) of macaques and the feline immunodeficiency virus, both of which cause fatal AIDS-like diseases have been used in a number of vaccine trials and have provided much useful information. However, these viruses may not be related to HIV in all aspects and caution must be exercised in extrapolating successful results to the human situation. In any event, any promising vaccine tested in animals will ultimately still have to undergo rigorous trials in humans, a situation which could present ethical problems, and a possible shortage of volunteers (Matthews and Bolognesi, 1988).

In general, then, it is preferable to try to employ derivatives of the human virus, rather than rely on results from animals. Some advantages and disadvantages of HIV AIDS vaccine design are as follows.

Live recombinant vaccines would be simple to prepare, but safety would be a major concern, especially as there is low immunogenicity requiring a high antigenic load, adjuvants and multiple doses. Accordingly, this approach is considered unlikely to provide any future vaccine.

A sub-unit vaccine, comprising either native or recombinant sub-units might be safe, but would be limited because of the choice of sub-units and low immunogenicity. Synthetic peptides suffer from similar problems, and this applies even more to chimeric vaccines with HBs or Polio, for example, where there is a choice of epitope.

Because of their complete safety, sub-unit vaccines can be used directly in human trials (Koff and Hoth, 988, Dolin et al., 1991), and are an important research tool in investigating the human immune response to particular epitopes. Glycoprotein vaccines have been shown to elicit humoral and cellular immune responses in man and animals (Arthur et al., 1987; Dolin, 1991), but challenge experiments with chimpanzees have not shown complete protection (Berman et al., 1988; Berman et al., 1990).

Nevertheless, most attention has so far been focused on the external envelope glycoprotein, either native (Arthur et al., 1987), recombinant (Anderson et al., 1989; Page et al., 1990; Smith and Volvoritz, 1990; Dolin et al., 1991) or synthetic (Ciba-Geigy Ltd, Switzerland).

Whole virus vaccines have been tried in the simian model (Marx et al., 1986; Desrosier's et al., 1989; Murphey-Corb et al., 1989; Stott et al., 1990), and found to be relatively successful, but this approach is not preferred because of the potential dangers.

Scientific opinion on the whole virus vaccine approach in HIV ranges from "Using antigenic sub-units rather than the pathogen itself would be preferable because they eliminate the threat of inadvertent infection", (Matthews and Bolognesi, 1988) through "Immunisation with killed preparations of whole HIV or sub-units thereof may not be safe or practical", (Berzofsky, 1988) to "Little serious consideration has been given to using preparations containing the virus as a vaccine. A vaccine must consist of sub-units", (Gallo and Montagnier, 1988), and "It must be emphasised that a disrupted, inactivated virus preparation would not be practical for use in humans", (Desrosier, 1989), as well as "A killed virus vaccine is unlikely because it is difficult to ensure that virus is completely inactivated", (Minor, 1989).

Thus, the main reason for reluctance to investigate the use of inactivated HIV virions is one of safety. Although safer than live attenuated vaccines, there is always the possibility that an inactivated-virion vaccine would contain some infectious virus which evaded the inactivation process.

The existence of such a problem was first realised in the 1950's when an incompletely inactivated batch of the polio vaccine was released for use (Nathanson and Langmuir, 1963). Although the importance of removing virus aggregates prior to chemical inactivation had already been highlighted (Gard, 1960), it was probably failure of the inactivating agent to penetrate clumps of virus that led to this incident.

Traditionally, inactivated vaccines have been produced with formaldehyde alone, as with the polio vaccine referred to above, and this method has been used in most of the SIV studies (Gardener, 1990).

The active component of aqueous formaldehyde, methylene glycol, reacts with both nucleic acids and proteins, primarily through exposed amino and imino groups and purines and pyrimidines. These interactions can lead to cross-linking of proteins, or tanning, which is thought to "lock up" the membrane, thereby restricting access to the susceptible nucleic acid (Gard, 1960).

A derivative of formaldehyde commonly used in routine inactivation of viruses is glutaraldehyde. Because of its highly reactive polar groups, it is active against enveloped viruses (Grint and Turner, 990). However, this agent, when employed at the concentrations used routinely (2% by volume), is not ideal for vaccine preparation, as it has some effect on the antigenicity and structure of the virions. Indeed, although it is commonly used as a fixative for electron microscopy, Sanger et al., (1973) warn that for some viruses, such as foot and mouth disease virus (FMDV), structural integrity can be severely impaired.

An alternative inactivating agent, now used in influenza, rabies and FMDV vaccine production, is α-propiolactone (BPL), the properties of which are outlined in Supplementary Example A. One of the major advantages of this agent is that it is completely hydrolysed to a non-toxic degradation product normally found in the body.

BPL has a long history of use as a viral inactivant for vaccine production (LoGrippo, 1960) and as a sterilant for plasma, whole blood (Hartman et al., 1954) and hospital equipment (Hooper, 1961). BPL reacts with electron dense atoms such as nitrogen in amines, amino acids and nucleic acids, causes mispairing, extensive cross linking and eventual breakage of DNA or RNA chains. A number of studies have shown that inactivation with β-propiolactone does not impair antigenicity or interfere with haematological, biochemical or serological investigations (Fellows, 1966; Chaplin et al., 1989; Ball and Griffiths, 1985; Ball and Bolton, 1985, Dooley et al., 1985; Freeman et al., 1982).

Examples of RNA viruses which have been inactivated with β-propiolactone include:

Polio I, II, III, 0.02% BPL, 2 hrs, 37° C.;

HIV-1, 0.14% BPL, 4 hrs, RT;

Coxackie virus, 0.25% BPL, 1 hr, RT;

Lassa fever virus, 0.2% BPL, 18 hrs at 4° C./30 mins at 37° C.;

FMDV, 0.05% BPL, ±UV, >20 hrs, 23° C.

Despite its advantages, the use of β-propiolactone alone still holds the possibility of residual live virus remaining after inactivation. Fellows (1966) demonstrated a "tailing off" curve for FMDV inactivated with 0.05% β-propiolactone at 23° C. Fellows overcame this problem by incorporating UV light into the inactivation system which gave rapid and complete inactivation but which impaired immunogenicity to a greater extent, and also required that the virus be exposed to the UV in thin films, a method unsuitable for bulk production.

Lloyd et. al., (1982) demonstrated that the β-propiolactone reaction is much more effective at 37° C., at which temperature Lassa fever virus was reduced from $10^7$ TCID 50 to undetectable levels in under 30 mins. However, because hydrolysis of β-propiolactone to its non-toxic derivative is also rapid at this temperature, there is still a possibility of undetected infectious virus remaining. For this reason, it is now common for the inactivation step with β-propiolactone to be repeated in most inactivation protocols.

An alternative to formaldehyde and β-propiolactone, with a long history of use in animal vaccines, is the ethylenimines (EI), the properties and uses of which are exemplified in Supplementary Example B.

RNA Viruses which have been inactivated with ethylenimines (AEI—acetyl-ethlenimine, or BEI—binary ethylenimine) include:

FMDV, AEI, 0.05%, 37° C., 4 hrs;

FMDV, BEI, 0.01M, 37° C., 24 hrs;

Pseudorabies (DNA), BEI, 0.001M, 37° C., 6 hrs;

Maedi-visna, BEI, 0.2%, 24° C., 24 hrs;

VSV, BEI, 0.001M, 37° C., 8 hrs;

Bovine Rhinotracheitis (DNA), BEI, 0.001M, 37° C., 8 hrs; and

Rabies virus, BEI, 0.01M, 37° C., 2 hrs.

Ethylenimines inactivate viruses by reacting with nucleic acids in a first order reaction (Larghi and Nebal, 1980; Bahnemann, 1974). Brown and Crick (1959) showed that these compounds produce vaccines far superior in safety and antigenicity than those inactivated with formalin, and ethylenimines have since been used for worldwide production of FMDV vaccines. Originally, acetyl-ethylenimine (AEI) was used but, as it is unstable, has a very low boiling point (Fellows, 1966) and is very toxic, it was replaced by the more stable, less toxic binary-ethylenimine (Bahnemann 1975).

Binary-ethylenimine (BEI) is formed by the cyclisation of 2-haloalkylamines under alkaline conditions, which reaction can be carried out either in the virus suspension, or separately, prior to addition. As Bahnemann (1975) showed that the latter method gave more rapid inactivation and that binary ethylenimine could be stored at 20° C. for 2 months without loss of activity, this is the currently preferred method.

Other inactivating agents have been used, either alone, or in combination with those above, but generally as a measure to combat the interfering effects of proteins in plasma and sera where these products need to be rendered free of virus before undergoing biological assays. The combination of UV light and β-propiolactone has been described above.

Another effective combination used against enveloped viruses is that of solvents and detergents such as tri(n-butyl) phosphate and sodium cholate (Edwards et al., 1987) which have very little effect on proteins. Such double combinations have been used in vitro for a simultaneous effect, to enhance the overall efficacy of the inactivating preparation.

Sequential use of two agents has been described (Rowlands et al., 1972), wherein FMDV was stabilised by formaldehyde before the application of acetyl ethylenimine as an inactivating agent, to retain protein and nucleic acid structure.

Useful components involved in the preparation of vaccines are not necessarily associated with preparation of the antigenic component. In particular, it is often useful to employ an immunopotentiating agent, or adjuvant, to enhance the antigenic effect. The most efficient immunopotentiating agent in experimental use is Freund's complete adjuvant (FCA), consisting of a water-in-oil emulsion of mineral oil, with mycobacteria suspended in the oil phase. This is not suitable for inclusion in human vaccines because of the various associated adverse side-effects, such as granuloma formation.

The only adjuvant licenced for use in humans is aluminium salts (alum). However, alum is ineffective with influenza HA and several other antigens, and does not consistently elicit cell mediated immunity. There is, therefore, a need to develop adjuvants with the efficacy of FCA but without the side effects.

Thus, there has been a substantial investigation into satisfactory alternatives. In particular, the adjuvant activity of mycobacteria in FCA has been localised to the peptidoglycan components of the cell wall, and can be reproduced with the synthetic analogue muramyl dipeptide (MDP) (Ellouz et al., 1974). In the aqueous phase this component only elicits a humoral response—to stimulate delayed type hypersensitivity, it needs to be formulated with an oily vehicle. A commercial preparation (syntex) (Alison and Bayars, 1986) of threonyl MDP in an oil in water emulsion of squalene with the spreading agent pluronic 121 has been used extensively in trials (Sujupto et al., 1990; Desrosier's et al., 1989). Other effective molecules are surface active compounds, such as the quaternary amine dimethyl dioctadecyl ammonium bromide (Snippe et al., 1977), or the triterpene glycoside saponin; Scott et al., 1984).

The adjuvanticity of these compounds can be amplified by a variety of approaches, such as co-entrapment of antigen and a synergistic mixture of adjuvants in liposomes (phospholipid vesicles). A similar strategy is to form regular, multimeric immunostimulating complexes (ISCOMS) with antigens and lipids (Morein, 1988). ISCOMS have now been used widely as experimental adjuvants and, in Sweden, they are authorised for use in an influenza vaccine for horses. Saponin naturally forms particulate structures with proteins from enveloped viruses.

Saponin was first used as an adjuvant by Thibault and Richon (1936). The saponin, known as Quil A, was derived from the bark of the South American tree *Quillaia saponaria* and has been found to be most effective as an adjuvant. Quil A is a triterpene with 2 sugar chains attached. Other saponins may have a variety of glycoside structures and attached sugars, and most are a mixture of different molecular species. The toxicity of different saponins also varies, and it appears that the greatest toxic effect is related to the impurities in the preparation and also the experimental animal used.

The use of ISCOMS greatly reduces the requirement for saponin in vaccine preparation. Scott et al., (1985) did experiments to suggest that the adjuvant activity of saponin resided in the effect on antigen presenting cells, although it also enhances T-independent immunity. They also found that cholesterol-lecithin liposomes accompanying KLH immunisation did not inhibit the adjuvant effect of saponin, although its toxicity was neutralised.

SUMMARY OF THE INVENTION

Accordingly, it is an object of the invention to provide a safe vaccine against AIDS comprising inactivated whole virus.

It is a further object of the invention to provide a useful adjuvant therefor, preferably with similar or better activity than FCA.

We have discovered that the disadvantages of the prior art can be overcome by the use of a multistage inactivation procedure, carried out in the correct sequence, which can inactivate virions in such a manner that the possibility of contamination is effectively eliminated.

In a first aspect, the present invention provides a process for the preparation of virus particles for vaccines, comprising, in order, the steps of:

a) Treating the virus with a general inactivating agent;

b) Deaggregating the virus with a suitable solvent or detergent;

c) Treating the virus with an RNA and/or DNA inactivating agent; and d) Stabilising the virus with a suitable cross-linking agent.

DETAILED DESCRIPTION OF THE INVENTION

It will be appreciated that the present invention is applicable to any virus, particularly the enveloped viruses. However, where a virus is either not particularly dangerous in itself, or can efficiently be inactivated by an alternative one-step procedure, then it would not generally be appropriate to use the method of the present invention.

Accordingly, it is preferred to use the method of the present invention for the preparation of particularly dangerous viruses, of which HIV and the various strains thereof are especially preferred. In addition, particularly heat and/or chemical resistant viruses, such as scrapie and BSE, may be used in vaccines, if prepared by the method of the invention.

In addition, as it known that there exists a number of antigenic variants of HIV, it is preferred to apply the process of the invention to a representative selection of strains. In particular, enough strains should be chosen such that an immune response raised from the resulting vaccine will be suitable to target any infectious strain of HIV.

Selecting various appropriate strains of HIV can be done by any appropriate method known in the art. In particular, it may be appropriate to compare the gp120 protein, one of the major antigenic targets of any immune response against HIV.

The method of the present invention may be applied directly to a mixed batch of strains as described above, or may be applied individually to batches of single strains, and the results mixed.

62 -Propiolactone provides a useful initial inactivant, allowing safe handling and concentration of the virus, without altering its antigenic properties.

However, the initial treatment of the virus with a general inactivating agent may be with any appropriate inactivating agent but, for the purposes of the present invention, it is preferred that such agent is β-propiolactone. The treatment with β-propiolactone may be in any suitable manner known to achieve inactivation, and may be carried out at low temperatures or high temperatures, and either generating β-propiolactone in the reaction, or using pre-prepared β-propiolactone. In general, it is preferred to use pre-prepared β-propiolactone at higher temperatures, such as 37° C. or 40° C. Also, at such high temperatures, it is preferred to repeat the treatment with β-propiolactone before proceeding to the next stage. A suitable concentration of β-propiolactone is 0.1% v/v.

This first inactivation stage may be conducted on purified virus, but this is not generally necessary, and may be conducted on crude culture supernatant fluid. However, after such treatment, it is then preferred to purify the virus, and this may by done by any suitable technique, such as by spinning the virus on a sucrose cushion.

After purification of the virus, the next stage is to deaggregate the virus. As described above, this is particularly important for a dangerous virus, as any virus which escapes the inactivation is potentially infectious.

Deaggregation can be achieved by methods known in the art, and suitable solvents and detergents have been described above. The only specific requirement is that as many clumps of virus are broken up as possible. It will be appreciated that it is not possible to guarantee that all clumps are broken up, but it is preferred to use such agents as will ensure maximum disruption of the clumps. In particular, it may be preferable to use a combination of solvents and detergents to maximise the effect.

The deaggregation of the clumps of virus also has another beneficial side-effect, in that the substances used to achieve this result also tend to disrupt the virus, which helps in inactivation. Further, the compounds also lead to "ballooning" of the virus, which allows access of other substances to the viral core, which would otherwise be protected. "Ballooning" is thought to entail expansion of the viral envelope without actually destroying the envelope, thus creating pores through which other substances can freely pass. Under selected circumstances, such as those described herein, ballooning is reversible, insofar as the envelope substantially readopts its original proportions.

Once the viruses have been ballooned, the genetic material can be inactivated. As has been described above, there are various techniques for inactivating RNA and DNA, and it is preferred to use, in accordance with the present invention, an ethylenimine, such as binary ethylenimine or acetyl-ethylenimine, and, in addition, an RNAse and/or DNAse.

Because of its superior penetrating properties (Fellows, 1966) and its first order inactivation kinetics, binary ethylenimine is an ideal second stage inactivant to back up the action of β-propiolactone.

After this stage, the virus may then be stabilised with a suitable substance, such as formaldehyde or glutaraldehyde. Any other suitable substances may also be used, the purpose being to present, as far as possible, a more morphologically intact virus. More particularly, the intention is to present a virus which is as similar as possible to the original virus, but which is completely inactivated.

Because of the toxicity of saponin and its mixed composition, we investigated the immunostimulatory action of digitonin. Using a highly purified, soluble form of digitonin, we found, in preliminary experiments, that mice injected with digitonin-treated influenza virus survived after receiving considerable quantities (100 mg/kg) of digitonin, without ill effect.

We have also discovered that digitonin is a particularly useful adjuvant, and this forms a preferred aspect of the present invention, either in combination with the process of the invention, or otherwise. If used alone, digitonin may be used as a conventional adjuvant to enhance the immune response generated by a vaccine. For example, digitonin may be of particular use in influenza vaccines, and need only be added to the vaccine, although it may be incorporated in such a manner as to ensure that it is incorporated into the viral coat, for instance.

In the context of the process of the invention, digitonin may be incorporated at any useful stage, but it is preferred to incorporate it after inactivation of the genetic material, and before stabilisation of the virus.

The result of using digitonin at this stage is that it is incorporated into the viral envelope, serving further to disrupt the envelope and also to provide an adjuvant in situ.

Other adjuvants may also be used, as appropriate, such as FCA, if the vaccine is for administration to animals. For human applications, alum may be used. Also, as described above, it may be possible to use other suitable substances, such as MDP, such as threonyl MDP, in combination with a suitable oil, such as squalene, and, if required, a spreading agent, such as Pluronic 121.

Where appropriate, it may also be desirable to enhance the adjuvanticity with, for example, ISCOMS. Further, it may be appropriate to employ saponin as an adjuvant, especially where this can be effected in combination with cholesterol-lecithin liposomes.

In order to enhance the safety of the vaccines of the present invention, it is generally desirable to assay the various stages of the preparation. Suitable assay procedures include the rapid syncytium assay, which may be applied after the initial inactivation step.

Other safety assays include testing of the vaccine preparation for residual non-inactivated virus by co-cultivation with human PBMN cells. The preparations may also be assayed for any residual intact DNA or RNA. This may be done by any method known in the art, such as by PCR.

It may also be appropriate to test any vaccine prepared to ensure that the full range of antigens is present in the vaccine. This may be done by testing in an animal, for example, and then challenging the animal. However, this tends to be rather empirical, and is not preferred. A more preferred technique would be to provide an ELISA test, where antibodies against all of the desired antigens are provided. Other appropriate tests will be apparent to those skilled in the art, and such tests may include, for example, immunoblotting.

The preparations may also be standardized for immunogenicity by vaccination tests in small or large laboratory animals, if desired.

Accordingly, the most preferred embodiment of the present invention is as follows:

1) Adaptation of 'street' viruses to continuously propagated T-cell line such as CEM or H9.
2) Inactivation of crude culture supernatant fluid with 2 stages of β-propiolactone (0.1% v/v each at 40° C. for 18 hrs)
2a) Subsidiary testing for infectious virus by rapid syncytium assay in cell culture.
3) Centrifugation at 19000 rpm for 1 hr onto a sucrose cushion, to achieve virus purification. Virus should be morphologically intact.
4) Deaggregation, ballooning and further inactivation of virus with 0.05% cholate.
5) Inactivation of "opened" cores (wherein the term "opened" is used to denote cores which are accessible because the envelope is ballooned) with binary ethylenimine (0.01M at 37° C. for 18 hrs).
6) Inactivation of viral RNA and contaminating host cell DNA with RNAse and DNAse.
7) "Adjuvanting" (treating so as to provide an adjuvant effect in the final vaccine) and further virus disruption and inactivation with digitonin.
8) Stabilisation of virions with mild formaldehyde or glutaraldehyde (0.05% on ice for 4 hrs).
9) Testing of vaccine preparation for residual non-inactivated virus by co-cultivation with human PBMN cells for 6 weeks.
10) Analysis by polymerase chain reaction (PCR) for residual proviral DNA and viral RNA (additional step of reverse transcription to cDNA) using primers specific for viral reverse transcriptase and integrase.

11) Standardisation of vaccine by ELISA and immunoblotting with human post infection antisera, to ensure antigenic survival.

12) Standardisation of immunogenicity by vaccination tests in small or large laboratory animals.

Administration of the vaccines and treatments according to the present invention will vary according to the circumstances, taking into account such factors as age, weight and general condition of the patient.

The vaccine may be administered as one self-sufficient dose or as a series of doses over a period of time.

Repetition of dosing either to boost or maintain immunity is also generally desirable at a later time, conveniently about 3 months later, but such booster dosing may be given earlier or at any time during the remainder of the life-time of the patient, and on as many occasions are necessary.

Pharmaceutical grade saline may be used as a carrier to provide a simple vaccine. However, it may often be preferred to use adjuvants, such as described hereinabove.

In general, an adjuvant may be administered together with the vaccine, in the same or different preparations, or separately, at a time different from that of the administration of the vaccine.

Vaccines according to the present invention will usually be administered by a conventional route such as, for example, by injection by the intravascular, intraperitoneal, intramuscular or subcutaneous routes. Other suitable routes may comprise intradermal inoculation or administration via particulate aerosols.

Such vaccines will normally comprise a pharmaceutically acceptable carrier and optionally an adjuvant, substances to render the vaccine isotonic with the body fluids and such flavourings, emulsifiers and other ingredients as may be required.

Such vaccines as described above may be sub-divided for separate administration, whether simultaneously or over a period of time, suitably weeks.

In general, it will be appreciated that the type of vaccine and its ingredients will be determined by the virus concerned, and will often correspond to existing vaccines, the advantage lying in the safety of the preparation.

Thus, it will be appreciated that the present invention provides a unique combination of steps enabling a safe vaccine to be prepared from highly dangerous viruses. Of course, it will be appreciated that no vaccine can be absolutely guaranteed, but the present invention provides a vaccine whose benefits far outweigh the potential risks.

In general, preferred objectives of our procedure for producing a whole HIV vaccine are:

1) To incorporate a "cocktail", or selection, of viruses selected to match circulating wild type or "street" viruses on the basis of epidemiological features and antigenic and nucleotide sequence analysis of gp120 loop regions. Alternatively, fewer but "archetypal" (strains carrying selected distinctive viral characteristics) virus strains may be used.

2) To inactivate the viruses completely using a unique multistage chemical and biological process which will still maintain the structural integrity of the virus and hence the major antigenic determinants of both externally situated glycoproteins and core proteins.

3) To ensure appropriate immunogenicity of the inactivated vaccine preparation and to compare the immune response in laboratory animal models with the standard immune response following HIV infection of humans.

4) To adjuvant the vaccine.

5) To formulate the vaccine for both intramuscular and oral administration.

The combination of steps in the correct order is unique, as is the use of detergent ballooning and adjuvant (digitonin) incorporation into the virion lipid. The most important novel features of our procedure are probably:

1) Multiple inactivation steps—Current inactivated vaccines are killed using single chemical agents. Our method ideally utilises five independent inactivation steps (4 chemical and 1 biological) each one of which is individually able to inactivate the virus.

2) Correct sequence of chemicals—The order of inactivating steps is particularly important. Inactivating agents each have a specific target (virus protein, nucleic acid, virus envelope) and need to be used in the correct sequence, which we have established experimentally. For example, in the only published paper (Rowlands, 1972) a reverse sequence of two of the agents was used.

3) New Adjuvants—Digitonin, a saponin-like molecule, disrupts the lipid membrane of retroviruses. Digitonin in the virus preparation both disrupts and inactivates virus, while also enhancing immunogenicity.

4) Virus deaggregation and ballooning by cholates—The use of detergents (eg cholates), not to totally disrupt virus, but to deaggregate them and cause ballooning, hence allowing access of nucleic acid inactivating agents such as binary ethylenimine, is a preferred aspect of the invention. We have shown that RNA-containing viruses with lipid envelopes may be uniquely ballooned with the correct concentrations of detergent.

5) Nucleic acid destruction—Incorporation of RNAse and DNAse steps to inactivate contaminating proviral DNA from virus infected cells and virion RNA.

6) Enhanced penetration of inactivating agents—The further partial disruption of the virus by digitonin and disturbance of the lipid bilayer allows enhanced penetration of binary ethylenimine.

7) "Presentation shape" to the immune system—Formaldehyde or mild glutaraldehyde fixation allows presentation of antigens in a correct "presentation shape" (the 3-dimensional conformational features of the virus are substantially the same as untreated virus) for recognition by the immune system.

The following Examples illustrate the invention, and are not intended to limit the invention in any manner whatsoever.

EXAMPLE 1

Adjuvant activity of Digitonin

The following experiment is based on the assumption that a single dose of influenza vaccine would not induce protective immunity. Accordingly, if immunity can be demonstrated after the administration of only one dose, then it is extremely likely that any additional substance that had been incorporated into the vaccine has acted as an adjuvant.

Digitonin was tested for adjuvant activity in an experimental protocol, using the known adjuvant, alhydrogel, for comparison. Digitonin and alhydrogel were included in influenza vaccine preparations to investigate whether the combination could enhance immunity to a protective level. 14 g Balbc mice were immunised i.p. with a subunit influenza vaccine at 4 and 0.4 µg per mouse. Four weeks post immunisation, approximately $50LD_{50}$ of the homologous influenza virus was administered to each mouse, intranasally under light ether anaesthesia. Non-immunised mice were included as controls. Deaths were scored daily. Results are shown in the accompanying Table.

TABLE

Effect of subunit influenza vaccine versus infection with lethal influenza virus

| Vaccine preparation | No. of dead mice (5 mice per cage) |
|---|---|
| Subunit vaccine alone 4 μg | 4 |
| Subunit vaccine alone 0.4 μg | 4 |
| Subunit vaccine plus alhydrogel 4 μg | 1 |
| Subunit vaccine plus alhydrogel 0.4 μg | 3 |
| Alhydrogel alone | 4 |
| Digitonin (0.1%) alone | 4 |
| Digitonin (0.01%) alone | 5 |
| Subunit vaccine plus digitonin (0.1%) 4 μg | 0 |
| Subunit vaccine plus digitonin (0.1%) 0.4 μg | 0 |
| Subunit vaccine plus digitonin (0.01%) 0.4 μg | 0 |

The results clearly demonstrate that one dose of non-adjuvanted vaccine offers no protection against infection. Alhydrogel had little or no adjuvant activity with the lower dose vaccine, and could not save all mice even at the higher dose. By contrast, digitonin saved all mice at all concentrations tested, even with the 0.4 μg vaccine.

EXAMPLE 2

Inactivation of HIV with Betapropiolactone and Binary ethylenimine

TABLE 1

Inactivation of concentrated HIV with β-propiolactone.
Virus was concentrated by PEG precipitation to give a high titre. Virus was treated with various concentrations of β-propiolactone at room temperature for 24 hours then assayed for residual infectivity.

| Log 10 TCID of virus per ml | Concentration of BPL |
|---|---|
| 8.0 | 0.0% |
| 5.0 | 0.01% |
| 2.0 | 0.05% |
| 1.0 | 0.5% |
| 0.0 | 1.0% |
| 0.0 | 2.0% |

TABLE 2

Inactivation of unconcentrated HIV by β-propiolactone.
Virus in tissue culture supernatant was treated with various concentrations of β-propiolactone at room temp for 24 hours then assayed for residual infectivity.

| Log 10 TCID of virus per ml | Concentration of BPL |
|---|---|
| 5.0 | 0.00% |
| 4.0 | 0.002% |
| 2.0 | 0.004% |
| 0.0 | 0.008% |
| 0.0 | 0.016% |
| 0.0 | 0.03125% |
| 0.0 | 0.0625% |
| 0.0 | 0.125% |
| 0.0 | 0.25% |

TABLE 2-continued

Inactivation of unconcentrated HIV by β-propiolactone.
Virus in tissue culture supernatant was treated with various concentrations of β-propiolactone at room temp for 24 hours then assayed for residual infectivity.

| Log 10 TCID of virus per ml | Concentration of BPL |
|---|---|
| 0.0 | 0.5% |
| 0.0 | 1.0% |
| 0.0 | 2.0% |

TABLE 3

Time course of inactivation of HIV with β-propiolactone.
Concentrated HIV was treated with 0.2% β-propiolactone and the reaction stopped at various time intervals by incubation at 37° C. for 30 mins to hydrolyse the β-propiolactone.

| Log 10 TCID of virus/ml | Time (hours) |
|---|---|
| 8.0 | 0 |
| 6.0 | 0.5 |
| 5.0 | 1 |
| 4.0 | 2 |
| 2.0 | 3 |
| 2.0 | 4 |
| 1.0 | 5 |
| 0.0 | 6 |

TABLE 4

Inactivation of HIV with binary ethylenimine.
Concentrated HIV was treated with different concentrations of binary ethylenimine at 37° C. for 24 hours. Residual binary ethylenimine was neutralised with sodium thiosulphate and the virus tested for infectivity.

| Log 10 TCID of virus/ml | Concentration of BEI (mM) |
|---|---|
| 8.0 | 0 |
| 8.0 | 0.1 |
| 7.0 | 0.5 |
| 4.0 | 5 |
| 0.0 | 10 |
| 0.0 | 20 |
| 0.0 | 50 |

TABLE 5

Time course of inactivation of HIV with binary ethylenimine.
Concentrated HIV was treated with 10mM binary ethylenimine. Aliquots were taken at various time intervals, neutralised with sodium thiosulphate and assayed for residual infectivity.

| Log TCID of virus/ml | Time (hours) |
|---|---|
| 8.0 | 0 |
| 6.0 | 1 |
| 5.0 | 2 |
| 4.0 | 3 |
| 3.0 | 4 |
| 2.0 | 5 |
| 1.0 | 6 |
| 0.0 | 7 |
| 0.0 | 8 |

EXAMPLE 3

Immunogenic Studies

Preliminary studies on the immunogenicity of the vaccine were carried out in rats, guinea pigs and rabbits.

Animals were intravenously immunised with 100 μg (total protein in 0.5 ml PBS) per animal of either:

1) β-propiolactone inactivated virus or
2) Virus inactivated by the full vaccine production process.

Animals were boosted on days 10 and 60 and serum samples were taken on days 0, 19, 52 and 72. Serum antibodies were assayed by solid phase ELISA to whole virus and gp120 and by radioimmunoassay to gp120 derived peptides.

TABLE 6

Serum responses to whole HIV RF and HIV IIIB derived gp120 (expressed as endpoint titres).

| Vaccine | Animal | Antibody titre Whole RF | IIIB gp120 |
|---|---|---|---|
| Vaccine 1 (BPL only) | Rat 1 | 45,000 | 1,000 |
| | Rat 2 | 400,000 | 1,200 |
| | Rat 3 | 400,000 | 1,000 |
| | Rat 4 | 100,000 | >10,000 |
| | Guineapig 1 | 700,000 | 25,000 |
| | Guineapig 3 | 74,000 | 25,000 |
| | Guineapig 4 | 74,000 | 1,800 |
| | Rabbit 1 | 20,000 | 20,000 |
| | Rabbit 2 | 74,000 | >25,000 |
| Vaccine 2 (complete process) | Rat 5 | 450,000 | 400 |
| | Rat 6 | 250,000 | 160 |
| | Rat 7 | 16,000 | >10,000 |
| | Rat 8 | 800,000 | >10,000 |
| | Guineapig 5 | 10,000 | 3,000 |
| | Guineapig 6 | 100,000 | 25,000 |
| | Guineapig 7 | 450,000 | 10,000 |
| | Guineapig 8 | 80,000 | 3,600 |
| | Rabbit 3 | 74,000 | 6,000 |

Radio immunoassay studies on the guineapig sera showed responses to the V2 and V3 loop areas of HIV RF gp120 in both groups of animals (vaccine 1 and vaccine 2).

SUPPLEMENTARY EXAMPLE A

Properties of Beta-Propiolactone i) Synonyms—BPL; Hydracrylic acid β-Lactone; 2-Oxetanone; Propanolide; 3-hydroxypropionic acid β-Lactone; β-propiolactone; Betaprone ii) Empirical formula—$C_3H_4O_2$, mol. wt. 72.1 iii) Melting point—33.4° C.; Boiling point −162° C.

iv) Solubility—37% v/v at 25° C. in water (slowly hydrolyses). Miscible with ethanol (reacts), acetone, ether, chloroform, and probably most polar organic solvents and liquids.

v) Stability—polymerises on storage, hydrolyses to 3-hydroxy propionic acid, a non-toxic derivative, approx. 18% per hour at 25° C., more rapidly at elevated temperatures.

SUPPLEMENTARY EXAMPLE B

Properties of Ethylenimine i) Miscible with water and most organic liquids.
ii) Ring structure quantitatively opened by thiosulphate.

iii) Substitution of alkyl groups at one of ring carbon atoms increases rate of ring opening.

iv) Substitution at ring nitrogen decreases rate of ring opening unless alkyl group contains an electronegative group (e.g. acetyl) when rate is increased.

v) Common derivatives have low boiling points e.g. 56.7° C. for EI. Vapour pressure high enough to be an inhalation hazard.

vi) Ammonia—like odour.

vii) Ethylenimine is known to react with α and epsilon amino, imidazole, carboxyl, sulphydryl and phenolic groups of proteins, inorganic phosphate, glycero and hexose phosphates and amino groups of adenine and thiamine.

viii) Ethylenimine can be prepared by the cyclisation of bromoethylamine hydrobromide under alkaline conditions:

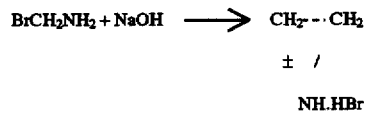

REFERENCES

1) Amadori, M., et al., Vaccine (1987), 5, 219;

2) Anderson, K. P., et al., J. Inf. Dis. (1989), 160 (6), 960;

3) Arthur, L. O., et al., Proc. Natl. Acad. Sci. USA (1987), 84, 8583–87;

4) Bahnemann, H. G., Vaccine (1990), 8, 299–303;

5) Bahnemann, H. G., Arch. Virol. (1975), 47, 47–56;

6) Bahnemann, H. G., J. Clin. Micro. (1976), 3 (2), 209–210;

7) Ball, M. J., and Bolton, F. G., Lancet (1985), II, 99;

8) Ball, M. J., and Griffiths, D., Lancet (1985), I, 1160;

9) Bolognesi, D., Annals of Internal Medicine (1991), 114 (2), 161;

10) Brown, F., and Crick, J., J. Immunology (1959), 82, 444–447;

11) Chaplin, A. J., et al., J. Clin. Path (1989), 42, 318–321;

12) Cutlip, R. C., et al., Vet. Microbiol. (1987), 13, 201–204;

13) Desrosier's, R. C., et al., Proc. Natl. Acad. Sci. (1989), 86, 6353–6357;

14) Dolin, R., et al., Annals of Internal Medicine (1991), 114(2), 119;

15) Dooley, B. J., et al., Med. Lab. Sci. (1985), 42, 318;

16) Durda, P. J., et. al., AIDS Res. and Human Retroviruses (1990). 6 (9), 1115;

17) Edwards, C. A., et al., Vox Sang. (1987), 52, 53–59;

18) Fellows, O. N., J. Immunology (1966), 95 (6), 1100;

19) Freeman, R., et al., Lancet (1982), May 8., 1048–49;

20) Gallo, R., and Montagnier, L., Scientific American (1988), 259 (4), 25;

21) Gard, S., Ann. N.Y. Acad. Sci. (1960), 83, 638;

22) Gardener, M. B., and Luciw, P. A., The FASEB Journal (1989), 3, 2593;

23) Gardener, M. B., AIDS Res. and Hu. Retroviruses (1990), 6(7), 835;

24) Grint, P., and Turner, G. S., Topley and Wilsons Principles of Bacteriology, Virology and Immunity (1990), Eight edition, vol. 4, p42, Eds Parker, M. T., and Collier, L. H.;

25) Hartman, F. W., et al., Am. J. Clin. Path. (1954), 24, 339;

26) Hooper, S. H., Amer. J. Hosp. Pharmacy (1961), 18 July, 388–391;

27) Koff, W. C., and Hoth, D. E., Science (1988), 2451, 426–432;

28) Larghi, O. P. and Nebal, A. E., J. Clin. Micro. (1980), 11 (2), 120–122;

29) Lloyd, G., et al., Lancet (1982), May 8, 1046–48;

30) LoGrippo, G. A., Annals N.Y. Acad. Sci. (1960), 83, 578;

31) Marx, P. A., et al., J. Of Virology (1986), 60 (2), 431–435;

32) Matthews, T. J., and Bolognesi, D., Scientific American (1988), October, 98;

33) Minor, P. D., J. Of Antimicrobial Chemotherapy (1989), 23 sup A, 55–62;

35) Murphey-Corb, M., et al., Science (1989), 246, 1293;

36) Nathanson, N., and Langmuir8r, A. D., Am. J. Hyg. (1963), 78, 16;

37) Page, M., et al., Vaccine (1990), 9, 47;

38) Prince, A. M., et al., Cancer Res. (1985), 45s, 492s–4594s;

39) Rowlands, D. J., et. al., Archiv. fur die gesamte virusforshung (1972), 39, 274–283;

40) Sanger, D. V., et al., J. Gen. Virol. (1973), 21, 399–406;

41) Schultz, P., et al., J. Immunology (1957), 79, 497–507;

42) Smith, G., and Volvoritz, F., VI International Conf. on AIDS Abstract S.A. (1990), 76, 114;

43) Sonigo, P., et al., Immunology Today (1990), 11 (12), 465;

44) Stephan, W., et al., Vox Sang., (1981), 41, 134–138;

45) Stott, E. J., et al., Lancet (1990), 336, 1538–41;

46) Sun, I. L., et al., J. Clin. Micro. (1978), 8(5), 604–611.

The above references are incorporated by reference herein.

What is claimed is:

1. A process for producing inactivated whole virus, the process comprising, in order, the steps of:
    a) treating a virus with a general inactivating agent;
    b) treating the virus with a suitable deaggregating agent;
    c) treating the virus with a suitable nucleic acid inactivating agent; and
    d) stabilizing the virus with a suitable cross-linking agent.

2. The process of claim 1, wherein the virus is selected from the group consisting of heat resistant viruses and chemical resistant viruses.

3. The process of claim 1, wherein the virus is selected from the group consisting of HIV, scrapie, BSE, influenza and strains thereof.

4. The process of claim 1, wherein the virus comprises a plurality of strains of the virus.

5. The process of claim 1, wherein treatment with the general inactivating agent is repeated.

6. The process of claim 1, wherein the general inactivating agent is β-propiolactone.

7. The process of claim 1, wherein the deaggregating agent is selected from the group consisting of solvents and detergents.

8. The process of claim 7, wherein the detergents are selected from the group consisting of tri (n-butyl) phosphate and sodium cholate.

9. The process of claim 1, wherein the nucleic acid inactivating agent comprises at least one agent selected from the group consisting of ethyleneimine, RNAse and DNAse.

10. The process of claim 9, wherein the ethyleneimine is selected from the group consisting of acetyl-ethyleneimine and binary-ethyleneimine.

11. The process of claim 1, wherein the cross-linking agent is selected from the group consisting of formaldehyde and glutaraldehyde.

12. The process of claim 1, wherein an adjuvant is added after treating the virus with the nucleic acid inactivating agent, and before stabilizing the virus with the cross-linking agent.

13. The process of claim 12, wherein the adjuvant is selected from the group consisting of digitonin, alum, saponin, Quil A, Freund's complete adjuvant, threonyl MDP, dimethyl dioctadecyl ammonium bromide and alhydrogel.

* * * * *